US008629688B2

(12) United States Patent
Chu et al.

(10) Patent No.: US 8,629,688 B2
(45) Date of Patent: Jan. 14, 2014

(54) METHOD FOR SULFUR-BASED CORROSION TESTING

(75) Inventors: King M. A. Chu, Fishkill, NY (US);
Steven R. Nickel, Rochester, MN (US);
Timothy J. Tofil, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 333 days.

(21) Appl. No.: 12/894,046

(22) Filed: Sep. 29, 2010

(65) Prior Publication Data

US 2012/0074968 A1    Mar. 29, 2012

(51) Int. Cl.
*G01R 27/08* (2006.01)
(52) U.S. Cl.
USPC .................... 324/700; 324/699; 324/716
(58) Field of Classification Search
USPC ....................................................... 324/700
See application file for complete search history.

(56) References Cited

U.S. PATENT DOCUMENTS

| | | | | |
|---|---|---|---|---|
| 2,878,354 A * | 3/1959 | Ellison | | 338/13 |
| 2,994,219 A * | 8/1961 | Schaschl | | 73/86 |
| 3,197,698 A * | 7/1965 | Schaschl et al. | | 324/700 |
| 3,331,021 A * | 7/1967 | Marsh et al. | | 205/775.5 |
| 3,340,727 A * | 9/1967 | Bracalente et al. | | 73/86 |
| 6,077,418 A * | 6/2000 | Iseri et al. | | 205/775.5 |
| 6,962,948 B2 * | 11/2005 | Ghoshal | | 522/31 |
| 7,553,901 B2 * | 6/2009 | Horikoshi et al. | | 524/588 |
| 8,232,812 B2 * | 7/2012 | Ankeney et al. | | 324/700 |
| 2006/0257672 A1 * | 11/2006 | Horikoshi et al. | | 428/447 |

FOREIGN PATENT DOCUMENTS

| | | |
|---|---|---|
| JP | 63173331 A1 | 7/1988 |
| JP | 1169925 A2 | 7/1989 |

OTHER PUBLICATIONS

Milton Farber and Donald M. Ehrenberg, High-Temperature Corrosion Rates of Several Metals with Hydrogen Sulfide and Sulfur Dioxide, Oct. 1952, IOURXAL of the Electro(',Hemical Society, vol. 99, Issue 10, pp. 427-434.*
Craig Hillman, Joelle Arnold, Seth Binfield, Jeremy Seppi, Silver and Sulfur: Case Studies, Physics, and Possible Solutions, Oct. 2007, DfR Solutions, College Park, MD, USA SMTA International, Oct. 2007.*
Kanji Otsuka, Yoshihisa Takeo, Hisashi Ishida, Takeo Yamada, Shigel Kuroda and Hiroshi Tachi, The Mechanisms That Provide Corrosion Protection for Silicone Gel Encapsulated Chips, Dec. 1987, IEEE Transactions on Components, Hybrids, and Manufacturing Technology, vol. CHMT-12, No. 4 pp. 666-671.*
Milton Farber and Donald M. Ehrenberg, High-Temperature Corrosion Rates of Several Metals with Hydrogen Sulfide and Sulfur Dioxide, Oct. 1952, ,IOURXAL of the Electro(Chemical Society, vol. 99, Issue 10, pp. 427-434.*
Malcolm L. White, Encapsulation of Integrated Circuits, Sep. 1969, Proceedings of the IEEE, vol. 57, No. 9, pp. 1610-1615.*

(Continued)

*Primary Examiner* — Jermele M Hollington
*Assistant Examiner* — Christopher McAndrew
(74) *Attorney, Agent, or Firm* — Steven L. Bennett (57) ABSTRACT

A method for performing corrosion testing is provided. The method includes applying a thin film of silicone to an electrical device to be tested, positioning the device in a chamber, connecting the device to electrical testing equipment for determining any change in electrical resistance of the device, and disposing a gaseous compound of sulfur in the chamber. The method also comprises monitoring the device for any change in electrical resistance for indicating failure of the device.

18 Claims, 7 Drawing Sheets

(56) References Cited

OTHER PUBLICATIONS

Giulio DiGiacomo, Metal Migration (Ag, Cu, Pb) in Encapsulated Modules and Time-To-Fail Model As a Function of the Environment and Package Properties, Reliability Physics Symposium, 1982. 20th Annual, Mar. 1982, pp. 27-33, Conference Publications.*

Abbott, William H., The development and performance characteristics of mixed flowing gas test environment, IEEE Transactions on Components, Hybrids, and Manufacturing Technology, Mar. 1988, vol. 11, Issue: 1, pp. 22-35.*

Thomas C. Hodge, et al., "Stresses in Thin Film Metalization", IEEE, 1997, pp. 241-, et al., IEEE, 1997, pp. 241-250.

Liang-Yu Chen, et al., "Thin and Thick Films Materials Interconnection Technology for 500 C Operation", NASA, Feb. 2000, pp. 1-10.

* cited by examiner

METHOD FOR SULFUR-BASED CORROSION TESTING

BACKGROUND

1. Field of the Invention

The present invention relates generally to corrosion testing, and more particularly to sulfur-based corrosion testing of electrical components.

2. Background Information

Sulfur is known to cause corrosion in electrical components having silver in the materials used for the components' fabrication and assembly. Because of its low cost and favorable electrical, chemical, and mechanical properties, silver finds many uses in electrical components. For example, silver is used as the base conductive element in thick film resistors or as a component of solder used to attach electrical components to printed circuit boards. Sulfur may be present in many different forms in the environments in which an electrical component may be used. Even relatively small concentrations of sulfur compounds such as hydrogen sulfide ($H_2S$) or sulfur dioxide ($SO_2$) may react with silver to form nonconductive sulfide corrosion products which may cause open circuit failures in electrical components. However, sulfur-based corrosion typically occurs very slowly. An electrical component may perform for years before it fails from sulfur-based corrosion.

Electrical components may be subjected to environmental tests in order to measure failure rates related to sulfur-based corrosion. Unfortunately, because of the relatively slow rate at which sulfur-based corrosion may occur, it may be difficult to obtain statistically significant failure results, even when components are exposed to sulfur compounds for hundreds of hours. So few test failures occur using known test methods that it may be difficult to correlate failure rates based on test results with actual field failures. Also, long duration tests are relatively expensive to perform. Higher temperatures may accelerate sulfur-based corrosion, so the time duration of an environmental test may be reduced by increasing a temperature at which the test is conducted. However, some electrical components may be damaged by exposure to temperatures that are high enough to cause a significant reduction in environmental test time when conventional test methods are used.

Electronic components may be protected from some forms of corrosion by coatings of relatively inert materials. For example, adhesives, potting compounds, and conformal coatings that include silicone polymers in their compositions are known to provide good protection from many different forms of chemical corrosion. However, coatings which include silicone polymers have been known to offer poor protection against sulfur-based corrosion.

BRIEF SUMMARY

In one general embodiment, a method for performing corrosion testing is provided. The method comprises coating an electrical component with a silicone film and exposing the component to a gaseous compound of sulfur to corrode the component. The method also includes counting a number of failures occurring in the component during exposure to the gaseous compound of sulfur for determining corrosion resistance of the component.

In another general embodiment, a method for applying a thin film of silicone to an electrical device to be tested is provided. The method comprises applying a thin film of silicone to an electrical device to be tested, positioning the device in a chamber, connecting the device to electrical testing equipment for determining any change in electrical resistance of the device, and disposing a gaseous compound of sulfur in the chamber. The method also comprises monitoring the device for any change in electrical resistance for indicating failure of the device.

In another general embodiment a method for coupling a thick film device to a test fixture. The method comprises coupling a thick film device to a test fixture, applying a layer of silicone film to the thick film device, positioning the thick film device and test fixture in a test chamber, connecting electrical leads to the thick film resistor and to electrical testing equipment for determining any change in electrical resistance of the device, exposing the thick film device to a selected concentration of vapors from flowers of sulfur for corroding the device for causing the device to fail, taking a plurality of electrical resistance measurements of the thick film device, and incrementing a count of failures when a measured value of electrical resistance is greater than a selected value of resistance corresponding to a test failure value. The method also comprises reporting each value of the count and each time at which the count was incremented.

DETAILED DESCRIPTION

The following description is made for the purpose of illustrating the general principles of the invention and is not meant to limit the inventive concepts claimed herein. Further, particular features described herein can be used in combination with other described features in each of the various possible combinations and permutations. Unless otherwise specifically defined herein, all terms are to be given their broadest possible interpretation including meanings implied from the specification as well as meanings understood by those skilled in the art and/or as defined in dictionaries, treatises, etc.

In one general embodiment, a method for performing corrosion testing is provided. The method comprises coating an electrical component with a silicone film and exposing the component to a gaseous compound of sulfur to corrode the component. The method also includes counting a number of failures occurring in the component during exposure to the gaseous compound of sulfur for determining corrosion resistance of the component.

In another general embodiment, a method for applying a thin film of silicone to an electrical device to be tested is provided. The method comprises applying a thin film of silicone to an electrical device to be tested, positioning the device in a chamber, connecting the device to electrical testing equipment for determining any change in electrical resistance of the device, and disposing a gaseous compound of sulfur in the chamber. The method also comprises monitoring the device for any change in electrical resistance for indicating failure of the device.

In another general embodiment a method for coupling a thick film device to a test fixture. The method comprises coupling a thick film device to a test fixture, applying a layer of silicone film to the thick film device, positioning the thick film device and test fixture in a test chamber, connecting electrical leads to the thick film resistor and to electrical testing equipment for determining any change in electrical resistance of the device, exposing the thick film device to a selected concentration of vapors from flowers of sulfur for corroding the device for causing the device to fail, taking a plurality of electrical resistance measurements of the thick film device, and incrementing a count of failures when a measured value of electrical resistance is greater than a selected value of resistance corresponding to a test failure value. The method also comprises reporting each value of the count and each time at which the count was incremented.

Figure 1:
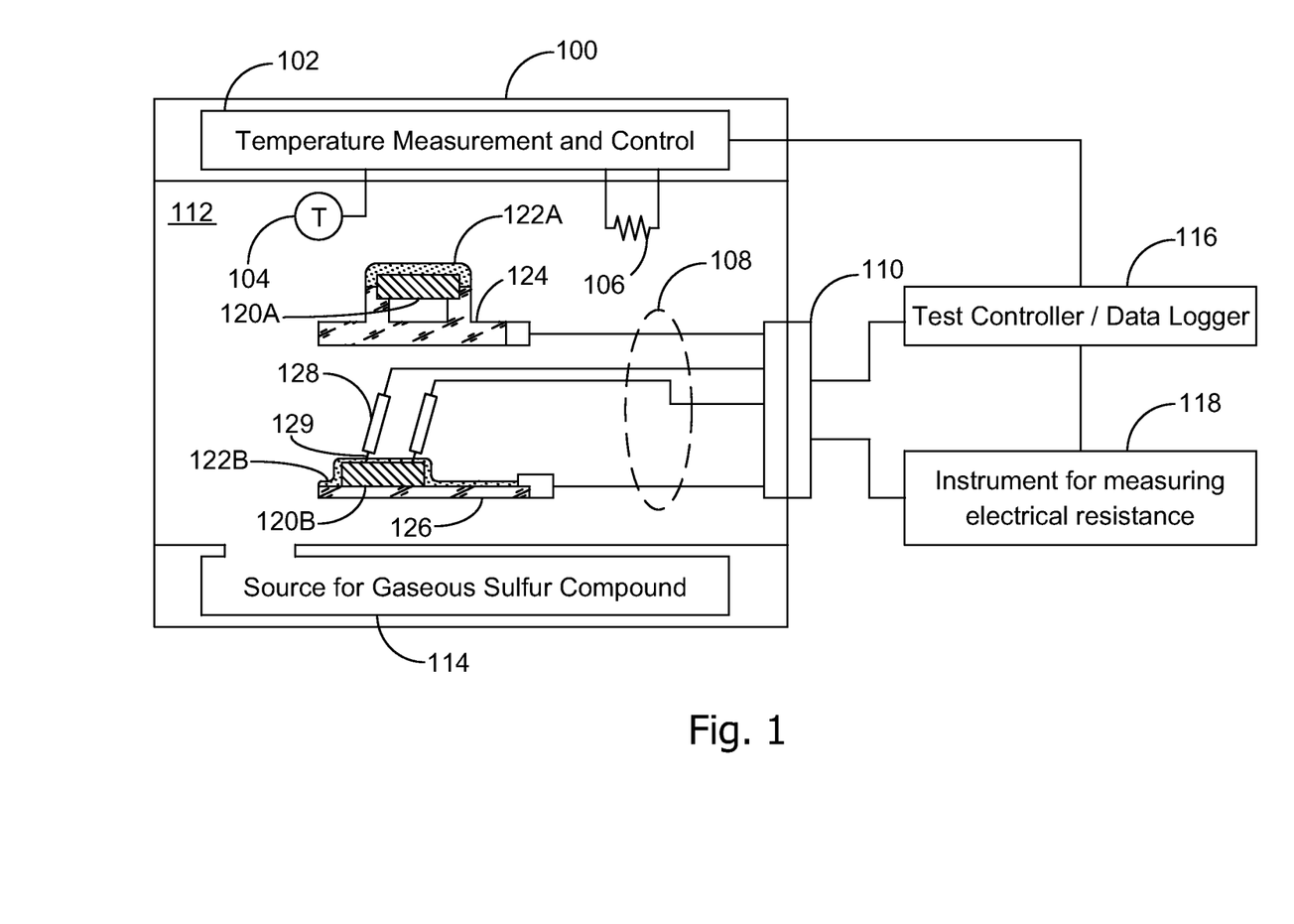
FIG. 1 illustrates an exemplary test apparatus for performing a corrosion test in accord with an embodiment of the invention.

Referring now to the Figures, an embodiment of equipment used to perform steps in an embodiment of a method for sulfur-based corrosion testing is shown in FIG. 1. It will be appreciated that many alternative equipment arrangements may be used instead of the arrangement shown in FIG. 1 to perform the disclosed method.

As shown in FIG. 1, an environmental test chamber 100 includes a temperature measurement and control system 102 connected to a temperature sensor 104 and heater 106 in the interior 112 of the test chamber. A test controller and data logger 116 may be used to change temperature set points for the temperature measurement and control equipment 102 according to a test schedule, record temperatures, make time interval measurements, record electrical measurements on an electrical component undergoing environmental testing, and make calculations using measured results. A source for a gaseous sulfur compound 114, for example a container of dry flowers of sulfur, may be placed inside the chamber 100 or may be connected to the interior 112 by conventional equipment for storing and controlling gaseous materials.

An electrical component 120 (shown in FIG. 3) undergoing corrosion testing, also referred to herein as a device under test (DUT) 120A, is shown attached to a test fixture 124. The test fixture 124 supports the DUT 120A inside the test chamber 100 and may make electrical connections between the DUT 120A and measurement and control equipment through an electrical interface 110. A plurality of electrical connections 108 may connect the test fixture 124 to the electrical interface 110. In one embodiment, instruments for measuring electrical parameters, such as an instrument for measuring electrical resistance 118 related to the DUT 120A, may be connected to the test fixture 124 though the interface 110. In one embodiment, an instrument for measuring resistance 118 includes a voltmeter, an ammeter, or an ohmmeter, or combinations of these instruments. Alternately, a DUT 120 may be a part of a printed wiring board assembly 126 as shown for a second DUT 120B. A selected number of electrical measurement probes 128 may be placed in electrical contact with the DUT 120B to make electrical measurements, such as resistance measurements. A probe 128 may have a tip 129 for penetrating a layer of silicone material to make electrical contact with a DUT 120.

In one embodiment, the DUT 120 has a coating of silicone material 122A covering the surfaces of the DUT 120 that will be exposed to a selected concentration of a gaseous compound of sulfur in the interior 112 of the test chamber 100. In one embodiment, the test fixture 124 is designed to penetrate a coating of silicone material 122A to make electrical contact with the DUT 120A. Alternatively, the test fixture 124 may be designed so that electrical connections to the DUT 120 are protected from coming into contact with the silicone material 122A. The second DUT 120B on the printed wiring board assembly 126 is also shown with a coating of silicone material 122B. In one embodiment, the entire printed wiring board assembly 126 may have a coating of silicone material 122B. Alternatively, the only the DUT 120B has a silicone material 122B coating.

Examples of silicone material 122 that may be used with an embodiment of the method include room temperature vulcanizing silicone rubber, also referred to herein as silicone RTV, silicone adhesive, silicone sealant, silicone conformal coat, or silicone in liquid form. The silicone material may be applied in a selected coating thickness by any suitable known means such as, brush, spatula, liquid droplet dispenser, syringe, metering fluid dispenser, roller, or via a tube with a nozzle, none of which are shown. When used in accord with an embodiment of the method, a silicone material coating substantially reduces an amount of time for a test failure related to sulfur-based corrosion to occur.

Figure 2:
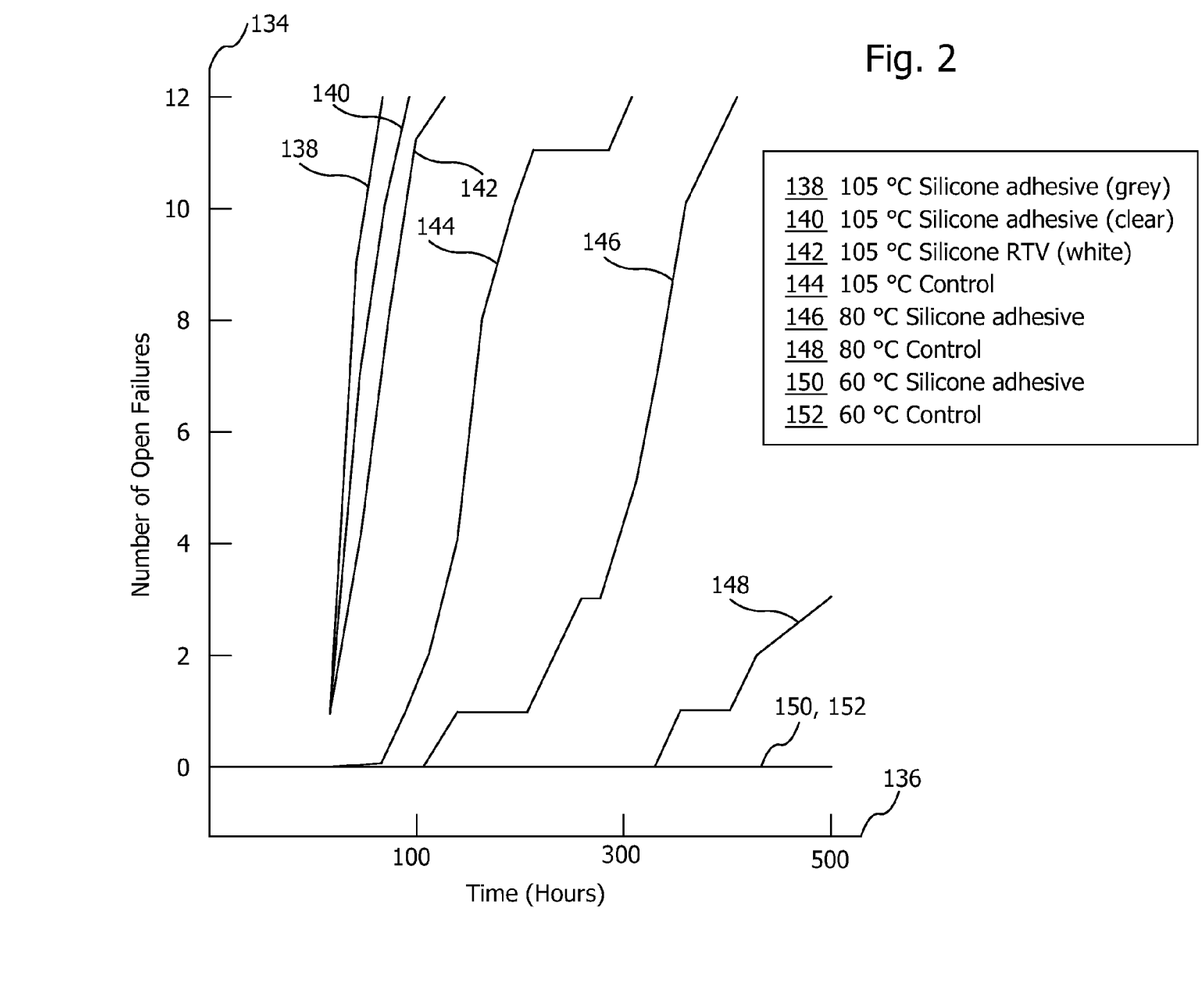
FIG. 2 illustrates a comparison of measured test results for electrical devices undergoing sulfur-based corrosion testing.

Referring to FIG. 2, exemplary corrosion test results for resistance measurements of thick film resistors exposed to vapor from dry flowers of sulfur in an environmental chamber operating at a specified temperature are shown. The test results are expressed as a count of the number of open circuit failures, "Open Failures", on a vertical axis 134 versus a test duration in hours on a horizontal axis 136. An "Open Failure" is recorded and a count of failures is incremented when a measured value of resistance indicates an open circuit in a DUT 120.

On Curve 138, a first failure occurs at approximately 60 hours for a resistor coated with grey silicone adhesive and exposed to vapor from dry flowers of sulfur at 105 degrees Celsius (° C.), increasing to 12 failures approximately 10 hours later. Curve 140 plots test failures for a DUT 120 coated with clear silicone adhesive and exposed to vapor from dry flowers of sulfur at 105° C. Curve 142 shows failures for a DUT 120 coated with white silicone RTV and exposed to vapor from dry flowers of sulfur at 105° C. Curve 144 shows a control test wherein an uncoated DUT 120 was exposed to vapor from dry flowers of sulfur at 105° C. Curves 146 and 148 show results for tests conducted at 80° C., and curves 150 and 152, which are nearly coincident with one another, for tests at 60° C. Coating a component with silicone material before conducting a sulfur-based corrosion test may reduce a time to failure by at least half compared to a similar test conducted without using silicone material. Preparations for conducting a test include coating a DUT with a thin layer of silicone material.

Figure 3:
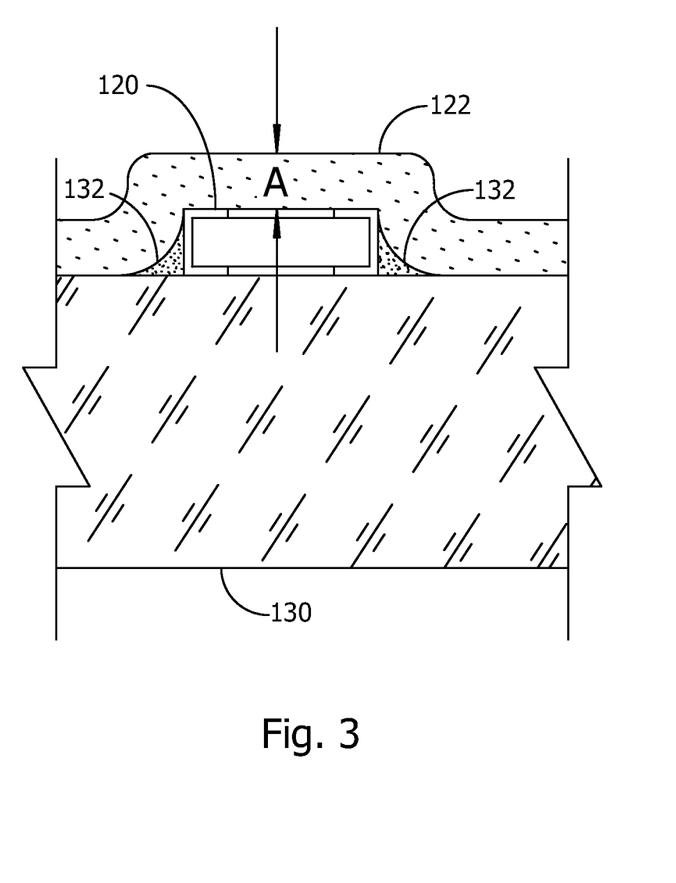
FIG. 3 illustrates an enlarged side view of a segment of a substrate, a component to be corrosion tested, and silicone polymer material layer.

Referring to FIG. 3, an enlarged side view of a component 120 covered with silicone material is shown. In one embodiment, the component 120 represents a thick film resistor. The component 120 may be connected by solder fillets 132 to a substrate 130. The substrate 130 is representative of either a test fixture 124 or a printed circuit board 126 (both shown in FIG. 1). A coating of silicone material 122 covers selected exposed surfaces of the component 120 and may cover other selected parts of the substrate 130 with a layer having a thickness dimension less than "A". In a preferred embodiment, the thickness "A" of a layer of silicone material is less than one millimeter.

Figure 4:
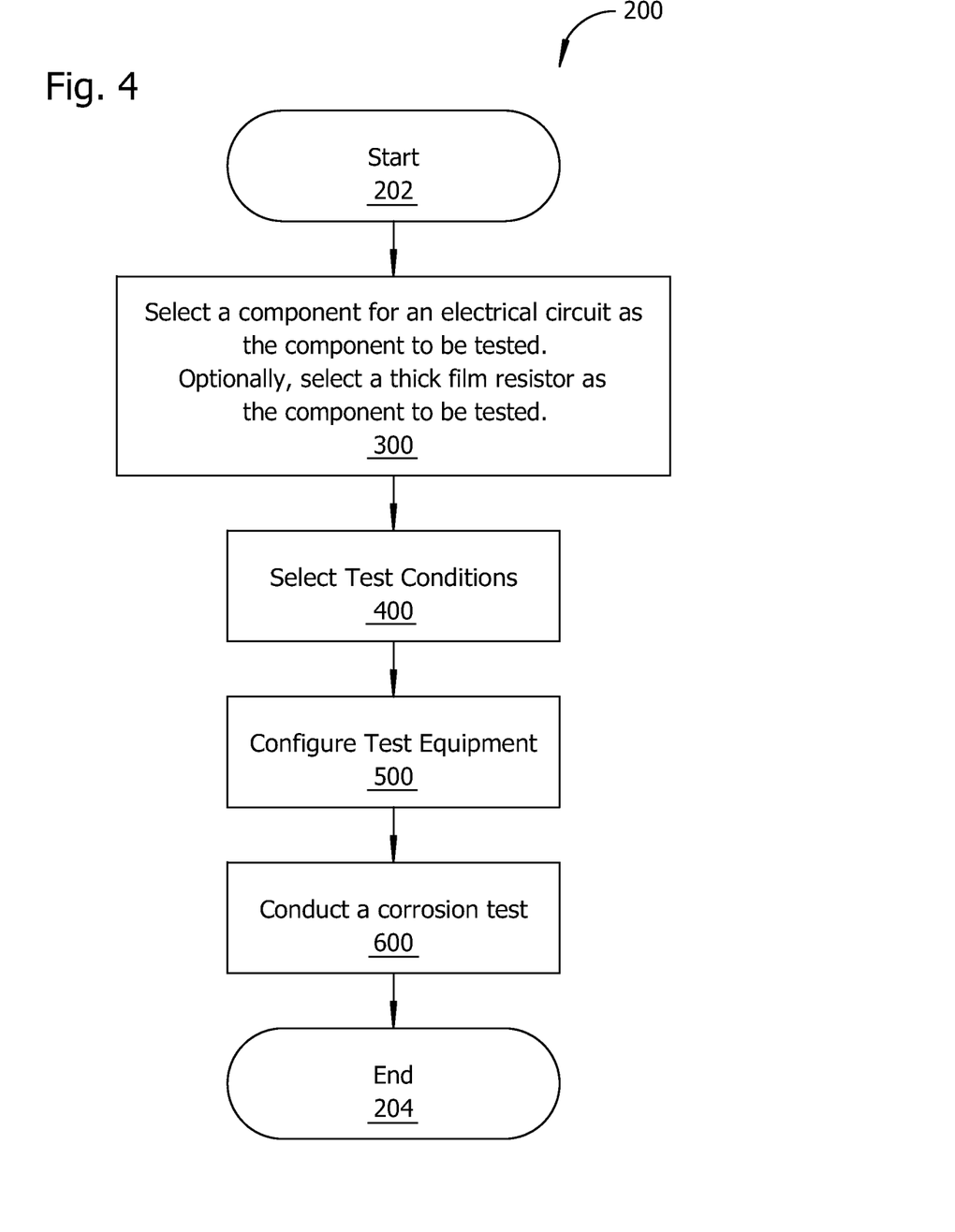
FIG. 4 illustrates a flow chart representing exemplary steps in a method for sulfur-based corrosion testing.

Exemplary steps in a corrosion test method 200 are illustrated in FIGS. 4-7. In FIG. 4, the method starts at step 202 and continues at step 300 with selection of a component 120 for an electrical circuit as the component to be tested, DUT 120. A thick film resistor may be selected as the DUT 120 to be tested. Next, test conditions are selected at step 400 and test equipment is configured for measuring electrical parameters related to the DUT 120 in step 500. A corrosion test is conducted at step 600 and the method ends at step 204.

Figure 5:
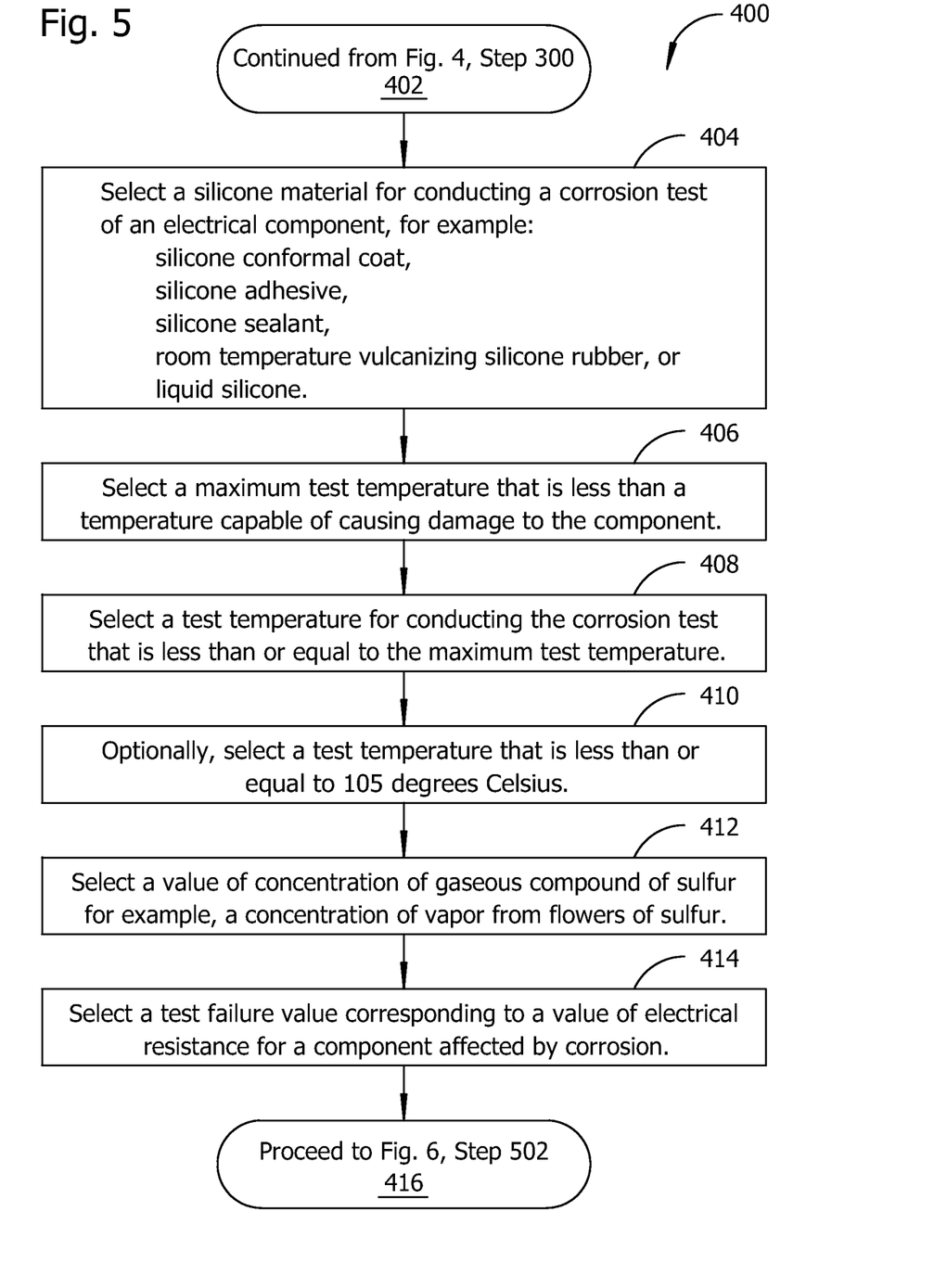
FIG. 5 illustrates a flow chart representing exemplary steps for selecting test conditions in the method of FIG. 4.

Referring to FIG. 1 and FIG. 5, FIG. 5 illustrates an embodiment of steps related to selection of test conditions at step 400 in FIG. 4. Selection of test conditions 400 begins at step 402 in FIG. 5 and continues with step 404 with selection of a silicone material for conducting a sulfur-based corrosion test of the DUT 120. At step 406, a maximum test temperature is selected. The maximum test temperature is preferably less than a temperature capable of causing damage to a DUT 120. At step 408, a test temperature for conducting the corrosion test is selected and is preferably less than or equal to the maximum test temperature selected in step 406. At step 410, a test temperature less than or equal to 105° C. may be selected. At step 412, a value of a concentration of a gaseous sulfur compound inside the test chamber is selected. At step 414, a test failure value is selected, for example, a value of resistance indicating that an open circuit fault has occurred in a DUT 120.

Figure 6:
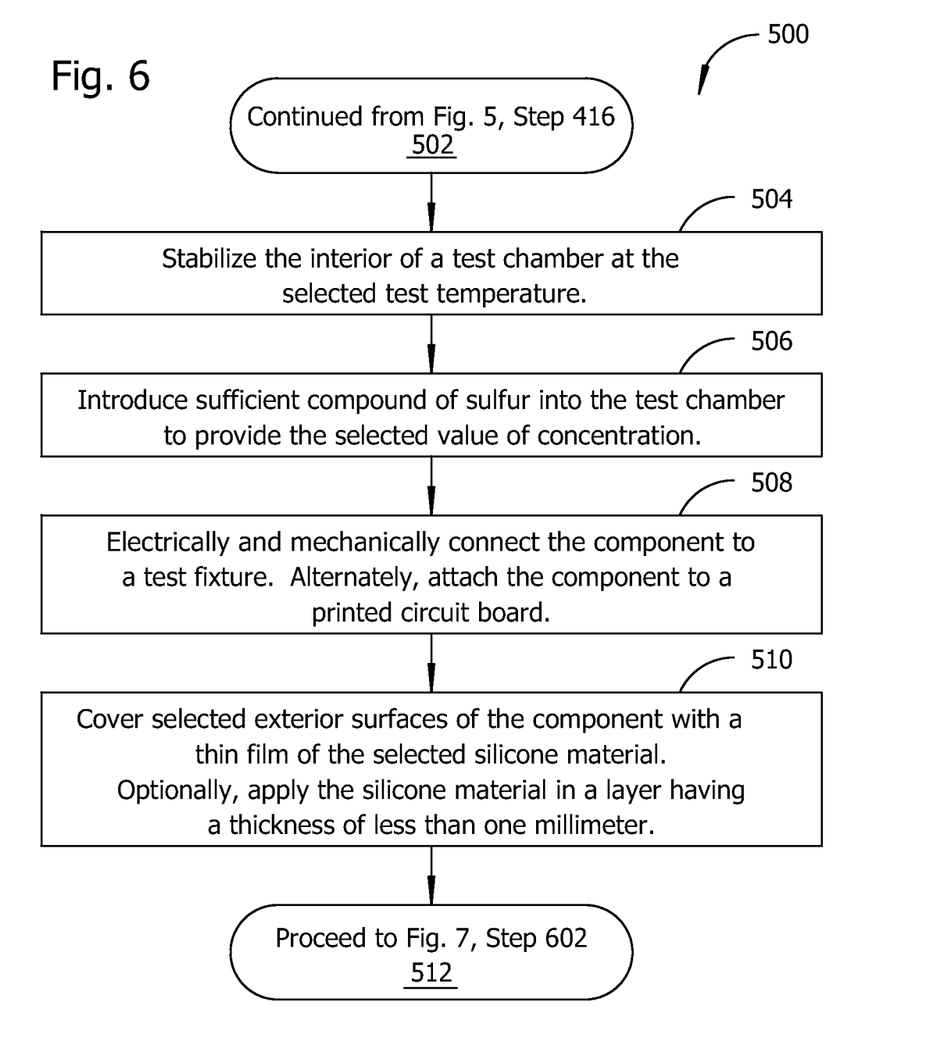
FIG. 6 illustrates a flow chart representing exemplary steps for configuring test equipment in the method of FIG. 4.

Referring to FIG. 1 and FIG. 6, FIG. 6 illustrates an embodiment of steps related to configuration of test equipment at step 500 in FIG. 4. Configuration of test equipment begins at step 502 in FIG. 6 and continues at step 504 with stabilization of the test chamber 100 at the test temperature selected in steps 408-410. Next, at step 506, sufficient sulfur compound is introduced into the interior of the test chamber 100 to establish the value of concentration selected in step 412. At step 508, a DUT 120 is connected to a test fixture 124. Alternately, the DUT may be attached to a printed circuit board 126 and tested as part of a printed wiring board assembly. At step 510, a layer of silicone material 122 is applied in a layer having a selected thickness to selected surfaces of the DUT 120. The silicone material 122 is preferably applied in a layer having a thickness of less than one millimeter (less than 0.04 inch) to the DUT 120.

Figure 7:
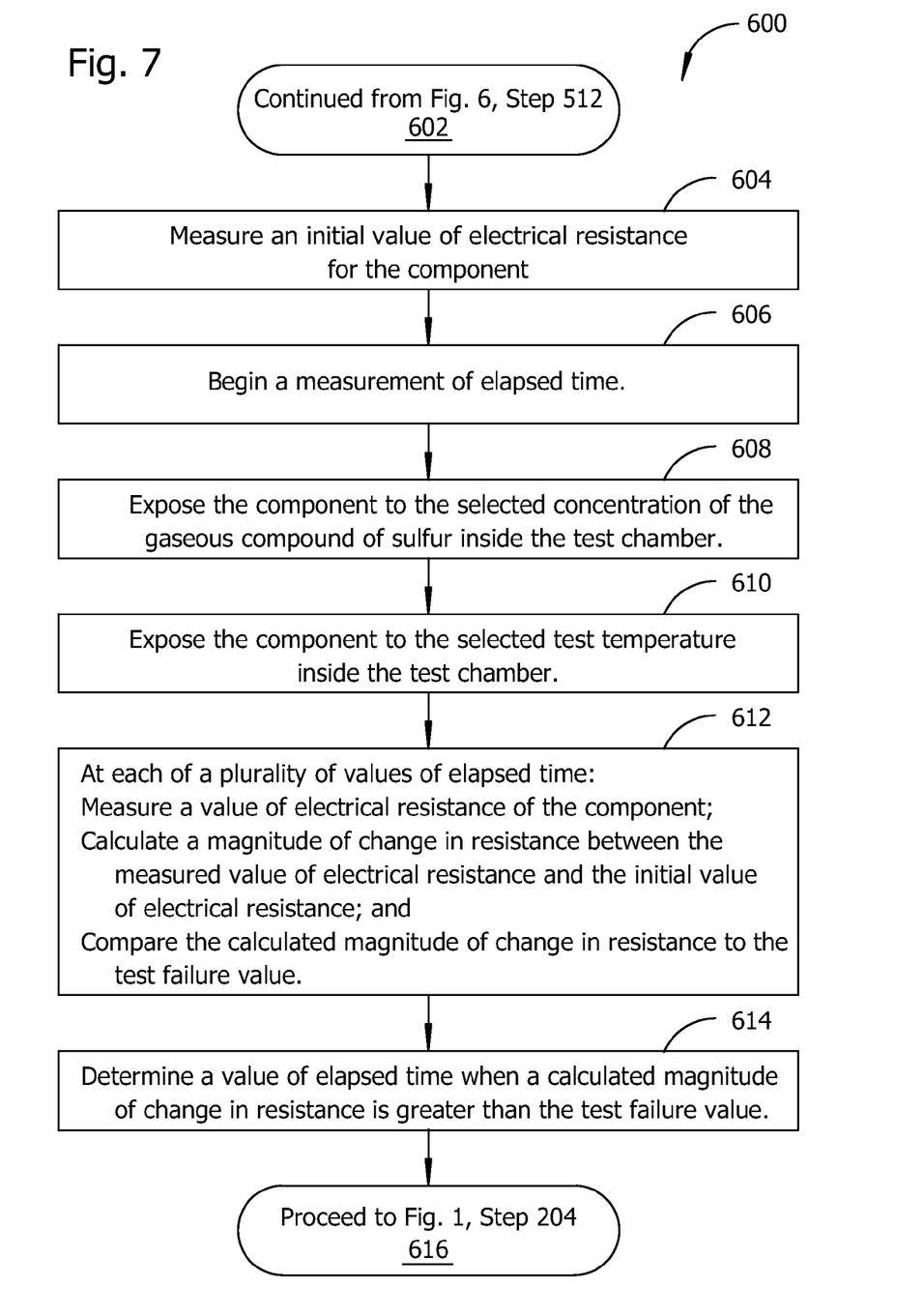
FIG. 7 illustrates a flow chart representing exemplary steps for conducting a corrosion test in the method of FIG. 4.

Referring to FIG. 1 and FIG. 7, FIG. 7 illustrates an embodiment of steps related to conducting a corrosion test at step 600 in FIG. 4. Corrosion testing beings at step 602 in FIG. 7 and continues at step 604 with measuring an initial value of electrical resistance for the DUT 120. A measurement of elapsed time begins at step 606, and concurrently with the start of the elapsed time measurement, the DUT 120 coated with silicone material 122 is exposed to the gaseous sulfur compound inside the test chamber at step 608 at the selected test temperature as shown in step 610.

A sequence of measurements is made at selected values of elapsed time in steps 612 and 614. At each selected value of elapsed time, a value of electrical resistance is measured for the DUT 120. A change in resistance from an initial value measured at step 604 is calculated and compared to the test failure value from step 414. A value of elapsed time at which a test failure occurs may be reported as a time to failure as indicated in step 614. A sulfur-based corrosion test may alternately continue for a predetermined length of time or until a first failure occurs.

Those skilled in the art will appreciate that various adaptations and modifications can be configured without departing from the scope and spirit of the embodiments described herein. Therefore, it is to be understood that, within the scope of the appended claims, the embodiments of the invention may be practiced other than as specifically described herein.

What is claimed is:

1. A method comprising:
    coating an electrical component with a silicone film for reducing an amount of time for a test failure of the component;
    exposing the component to a gaseous compound of sulfur to corrode the component; and
    counting a number of failures occurring in the component during exposure to the gaseous compound of sulfur for determining corrosion resistance of the component,
    wherein the electrical component is coated with the silicone film solely for sulfur-induced corrosion testing purposes to purposefully cause the electrical component to prematurely failure as a result of the sulfur-induced corrosion, where the electrical component is thereafter to be deployed in an actual usage environment without being coated with the silicone film.

2. The method of claim 1, wherein the silicone film reduces the amount of time for the test failure of the component to less than half of an amount of time for a test failure of the component without silicone film coating.

3. The method of claim 1, wherein the silicone film is selected from the group consisting of a room temperature vulcanizing silicone rubber, silicone sealant, silicone adhesive, and silicone conformal coating.

4. The method of claim 3, wherein the silicone film comprises one of a grey silicone adhesive and a clear silicone adhesive.

5. The method of claim 1, wherein the silicone film comprises a thin film of silicone with a thickness of approximately one millimeter.

6. The method of claim 5, wherein the thin film of silicone has a thickness of less than one millimeter.

7. The method of claim 1 further comprising:
    selecting a test temperature that is less than a temperature sufficient to cause damage to the component; and
    exposing the component to the test temperature.

8. The method of claim 7 further comprising: selecting a temperature that is less than or equal to 105 degrees Celsius.

9. The method of claim 1, wherein the electrical component is selected from the group consisting of a component for an electrical circuit and a thick film resistor.

10. A method comprising:
    applying a thin film of silicone to an electrical device to be tested for reducing an amount of time for a first test failure of the device;
    positioning the device in a chamber;
    connecting the device to electrical testing equipment for determining any change in electrical resistance of the device indicating the first test failure of the device;
    disposing a gaseous compound of sulfur in the chamber; and
    monitoring the device for any change in electrical resistance for indicating the first test failure of the device,
    wherein the electrical device is coated with the thin film of silicone solely for sulfur-induced corrosion testing purposes to purposefully cause the electrical device to prematurely failure as a result of the sulfur-induced corrosion, where the electrical device is thereafter to be deployed in an actual usage environment without being coated with the thin film of silicone.

11. The method of claim 10, wherein the thin film of silicone reduces the amount of time for the first test failure of the device to less than half of an amount of time for a test failure of the device without the thin film of silicone.

12. The method of claim 10, wherein the device is attached to a printed circuit board during measurement of electrical resistance of the device.

13. The method of claim 10 further comprising:
counting a number of failures occurring in the device during exposure to the gaseous compound of sulfur for determining corrosion resistance of the device.

14. The method of claim 13 further comprising:
retaining the device in a test fixture in the chamber during measurement of electrical resistance of the device;
measuring an initial value of electrical resistance of the device;
calculating a magnitude of change in resistance between a measured value of electrical resistance and the initial value of electrical resistance for determining the first test failure of the device; and
incrementing the count of failures when the measured value of electrical resistance is greater than the initial value of electrical resistance.

15. The method of claim 10 further comprising:
selecting a first test failure value;
comparing a calculated magnitude of change in resistance to the first test failure value; and
determining a value for a time to failure corresponding to a value of elapsed time when a calculated magnitude of change in resistance is greater than the first test failure value.

16. A method comprising:
coupling a thick film device to a test fixture;
applying a layer of silicone film to the thick film device for reducing an amount of time for a first test failure of the device;
positioning the thick film device and test fixture in a test chamber;
connecting electrical leads to the thick film resistor and to electrical testing equipment for determining any change in electrical resistance of the device indicating the first test failure of the device;
exposing the thick film device to a selected concentration of vapors from flowers of sulfur for corroding the device for causing the device to fail;
taking a plurality of electrical resistance measurements of the thick film device for determining any change in electrical resistance of the device indicating the first test failure of the device;
incrementing a count of failures when a measured value of electrical resistance is greater than a selected value of resistance corresponding to the first test failure value; and
reporting each value of the count and each time at which the count was incremented,
wherein the thick film device is coated with the silicone film solely for sulfur-induced corrosion testing purposes to purposefully cause the thick film device to prematurely failure as a result of the sulfur-induced corrosion, where the thick film device is thereafter to be deployed in an actual usage environment without being coated with the silicone film.

17. The method of claim 16, further comprising:
selecting a first test failure value;
comparing a calculated magnitude of change in resistance to the first test failure value; and
determining a value for a time to failure corresponding to a value of elapsed time when a calculated magnitude of change in resistance is greater than the first test failure value.

18. The method of claim 16, further comprising:
wherein the layer of silicone film reduces the amount of time for the first test failure of the thick film device to less than half of an amount of time for a test failure of the device without the layer of silicone film; and
wherein the film of silicone has a thickness of less than one millimeter.

* * * * *